(12) United States Patent
Chang et al.

(10) Patent No.: US 7,144,861 B2
(45) Date of Patent: *Dec. 5, 2006

(54) STABILIZED TERIPARATIDE SOLUTIONS

(75) Inventors: Chin-Ming Chang, Fishers, IN (US); Henry A. Havel, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 661 days.

This patent is subject to a terminal disclaimer.

(21) Appl. No.: 10/055,509

(22) Filed: Jan. 23, 2002

(65) Prior Publication Data
US 2002/0107200 A1   Aug. 8, 2002

Related U.S. Application Data

(63) Continuation of application No. 09/555,476, filed on May 31, 2000, now Pat. No. 6,770,623.

(60) Provisional application No. 60/069,075, filed on Dec. 9, 1997.

(51) Int. Cl.
*A61K 38/29* (2006.01)
*C07K 14/635* (2006.01)

(52) U.S. Cl. .................... 514/12; 530/325

(58) Field of Classification Search ............ 514/2, 514/12; 530/324

See application file for complete search history.

(56) References Cited

U.S. PATENT DOCUMENTS

| | | | |
|---|---|---|---|
| 4,698,328 A | 10/1987 | Neer et al. | |
| 5,496,801 A * | 3/1996 | Holthuis et al. | 514/12 |
| 5,607,915 A | 3/1997 | Patton | |
| 5,616,560 A | 4/1997 | Geddes et al. | |
| 5,891,086 A | 4/1999 | Weston | |
| 6,454,746 B1 | 9/2002 | Bydlon et al. | |
| 6,582,728 B1 * | 6/2003 | Platz et al. | 424/489 |
| 6,770,623 B1 * | 8/2004 | Chang | 530/325 |

FOREIGN PATENT DOCUMENTS

| | | |
|---|---|---|
| CA | 2 234 724 | 4/1998 |
| EP | 0 302 772 A1 | 2/1989 |
| EP | 0 490 806 | 6/1992 |
| EP | 0 619 119 A1 | 10/1994 |
| WO | WO 91/06564 | 5/1991 |
| WO | WO 94/08613 | 4/1994 |
| WO | WO 95/17207 | 6/1995 |
| WO | WO 99/5353 | 4/1998 |

OTHER PUBLICATIONS

Martin et al. "Effects of Benyzl alcohol on PTh receptor-adenylate cyclase system of canine kidney", American journal of physiology, (Jan. 1985) 248 (1 Pt 1) E31-5. 1985.*
Reeve et al., "Anabolic effect of human parathyroid hormone fragment on trabecular bone in involutional osteoporosis: a multicentre trial", Br. Med. J., 280(6228) :1340-1344, 1980.
Reeve et al., "Anabolic Effect of Low Doses of a Fragment of Human Parathyroid Hormone on the Skeleton in Postmenopausal Osteoporosis", The Lancet, 1:1035-1038, 1976.
Reeve et al., "Preliminary Trial of Low Doses of Human Parathyroid Hormone 1-34 Peptide in Treatment of Osteoporosis", Calcif. Tissue Res., 21:469-477, 1976.
Hodsman et al., "Biochemical responses to sequential human parathyroid hormone (1-38) and calcitonin in osteoporotic patients", Bone and Mineral, 9(2) :137-152, 1990.
Tsai et al., "Bone Responsiveness to Parathyroid Hormone in Normal and Osteoporotic Postmenopausal Women", J. Clin. Endocrinol Metab., 169(5) :1024-1027, 1989.
Isaac et al., "Absence of Effect of 1-34 h PTH on Plasma TSH, GH, FSH, LH, ACTH, and Cortisol in Normal Man", Horm. Metab. Res., 12(9) :487-488, 1980.
Law et al., "Rapid Development of Renal Resistance to Low Doses of Synthetic Bovine Parathyroid Hormone Fragment 1-34", J. Clin Invest., 72(3) :1106-1113, 1983.
Hulter et al., "Chronic Continuous PTH Infusion Results in Hypertension in Normal Subjects", J. Clin Hypertens, 2(4) :360-370, 1986.
Hodsman et al., "Bone densitometric and histomorphometric responses to sequential human parathyroid hormone (1-38) and salmon calcitonin in osteoporotic patients", 14(1) :67-83, 1991.
Martindale, The Extra Pharmacoepia, The Pharmaceutical Press, London, 29th Edition, 1989 p. 1338 (Copy not provided).

* cited by examiner

*Primary Examiner*—Anish Gupta
(74) *Attorney, Agent, or Firm*—Thomas D Webster; Brian P. Barrett; Steven P. Caltrider

(57) ABSTRACT

A stabilized pharmaceutical composition in the form of a solution for parenteral administration of a parathyroid hormone is described wherein the therapeutically active ingredient is stabilized with a buffer and a polyol. Preferred preparations contain in an aqueous solution human PTH (1–34), mannitol, an acetate or tartrate buffering agent and m-cresol or benzyl alcohol as a preservative.

15 Claims, No Drawings

STABILIZED TERIPARATIDE SOLUTIONS

This Application is a continuation of U.S. application Ser. No. 09/555,476, filed May 31, 2000, now U.S. Pat. No. 6,770,623, which claims benefit of U.S. Provisional Application No. 60/069,075, filed Dec. 9, 1997.

TECHNICAL FIELD

This invention relates to pharmaceutical compositions containing a parathyroid hormone. More particularly, the invention relates to teriparatide, PTH (1–34), stabilized solution formulations.

BACKGROUND OF THE INVENTION

Parathyroid hormone (PTH) is a secreted, 84 amino acid product of the mammalian parathyroid gland that controls serum calcium levels through its action on various tissues, including bone. Studies in humans with certain forms of PTH have demonstrated an anabolic effect on bone, and have prompted significant interest in its use for the treatment of osteoporosis and related bone disorders.

Using the N-terminal 34 amino acids of the bovine and human hormone for example, which by all published accounts are deemed biologically equivalent to the full length hormone, it has been demonstrated in humans that parathyroid hormone enhances bone growth particularly when administered in pulsatile fashion by the subcutaneous route. A slightly different form of PTH, human PTH(1–38) has shown similar results.

PTH preparations have been reconstituted from fresh or lyophilized hormone, and incorporate various forms of carrier, excipient and vehicle. Most are prepared in water-based vehicles such as saline, or water acidified typically with acetic acid to solubilize the hormone. The majority of reported formulations also incorporate albumin as a stabilizer (see for example Reeve at al., Br. Med. J., 1980, 280:6228; Reeve at al., Lancet, 1976, 1:1035; Reeve at al., Calcif. Tissue Res., 1976, 21:469; Hodsman et al., Bone Miner; 1990, 9(2):137; Tsai et al., J. Clin. Endocrinol Metab., 1989, 69(5):1024; Isaac et al., Horm. Metab. Res., 1980, 12(9):487; Law et al., J. Clin Invest. 1983, 72(3): 1106; and Hulter, J. Clin Hypertens, 1986, 2(4):360). Other reported formulations have incorporated an excipient such as mannitol, which is present either with the lyophilized hormone or in the reconstitution vehicle. Formulations representative of those employed for human studies include a human PTH(1–34) (SEQ ID NO:2) preparation consisting, upon reconstitution, of mannitol, heat inactivated human serum albumin, and caproic acid (a protease inhibitor) as absorption enhancer (see Reeve at al., 1976, Calcif. Tissue Res., 21, Suppl., 469–477); a human PTH(1–38) preparation reconstituted into a saline vehicle (see Hodsman et al., 1991, 14(1), 67–83); and a bovine PTH(1–34) preparation in aqueous vehicle pH adjusted with acetic acid and containing albumin. There is also an International Reference preparation which for human PTH (1–84) (SEQ ID NO: 1) consists of 100 ng of honnone ampouled with 250, μg human serum albumin and 1.25 mg lactose (1981), and for bovine PTH (1–84) consists of 10 μg lyophilized hormone in 0.01M acetic acid and 0.1% w/v mannitol (see Martindale, The Extra Pharmacoepia, The Pharmaceutical Press, London, 29th Edition, 1989 atp. 1338).

A recent attempt at improving the stability for the lyophilized preparation of h-PTH(1–34) (SEQ ID NO: 2) is reported in EP 619 119 with a combination of sugar and sodium chloride. Also U.S. Pat. No. 5,496,801 describes a freeze-dried composition for the natural hormone, PTH (1–84), containing mannitol as an excipient and a citrate source as a non-volatile buffering agent.

Commercial exploitation of parathyroid hormone requires the development of a formulation that is acceptable in terms of storage stability and ease of preparation. Because it is a protein and thus far more labile than the traditionally small molecular weight drugs, however, the formulation of parathyroid hormone-presents challenges not commonly encountered by the pharmaceutical industry. Furthermore, like other proteins that have been formulated successfully, PTH is particularly sensitive to oxidation, deamidation and hydrolysis, and requires that its N-terminal and C-terminal sequences remain intact in order to preserve bioactivity.

It is an object of the present invention to provide a pharmaceutically useful PTH preparation, particularly one comprising, as active ingredient, teriparatide, PTH(1–34) (SEQ ID NO: 2).

SUMMARY OF THE INVENTION

The present invention provides a pharmaceutical composition in the form of a stabilized solution containing a parathyroid hormone (PTH) in a therapeutically effective amount. The solution is storage stable and, in sterile form, may be stored in vials or cartridges ready for parenteral administration in human patients. The advantages of the present solution is the elimination of the need for lyophilization.

Accordingly, the present invention is a parathyroid hormone solution including:
  (a) a therapeutically effective amount of a parathyroid hormone;
  (b) an effective amount of a stabilizing agent;
  (c) a buffering agent in an amount sufficient to maintain the pH of the composition within a range of about 3–7; and
  (d) the balance being water.

This solution may, if desired, undergo lyophilization to form a freeze-dried powder containing not more than 2% water by weight.

Another aspect of the present invention is a parathyroid hormone solution including:
  (a) a therapeutically effective amount of a parathyroid hormone;
  (b) from about 1 to 20 wt-% of a stabilizing agent;
  (c) a buffering agent in an amount sufficient to maintain the pH of the composition within a range of about 3–7 and selected from an acetate or tartrate source;
  (d) from about 0.1 to 2 wt-% of a parenterally acceptable preservative; and
  (e) the balance being water.

Still another aspect of the present invention is a pharmaceutical composition in the form of a freeze-dried powder prior to reconstitution including:
  (a) a therapeutically effective amount of a fragmented parathyroid hormone selected from the group consisting of PTH (1–34), PTH (1–3 7), PTH (1–38), and PTH (1–41);
  (b) an effective amount of a stabilizing agent;
  (c) a buffering agent in an amount sufficient to maintain the pH of the composition within a range of about 3–7; and
  (d) less than 2% water by weight.

DETAILED DESCRIPTION

The invention relates to parathyroid hormone solutions that exhibit storage stability in terms of hormone composition and activity.

As active ingredient, the composition or solution may incorporate the full length, 84 amino acid form of parathyroid hormone, particularly the human form, hPTH (1–84) (SEQ ID NO: 1), obtained either recombinantly, by peptide synthesis or by extraction from human fluid. See, for example, U.S. Pat. No. 5,208,041, incorporated herein by reference. The amino acid sequence for hPTH (1–84) is reported by Kimura et al. in Biochem. Biophys. Res. Comm., 114(2):493 (SEQ ID NO: 1).

The composition or solution may also incorporate as active ingredient fragments or variants of fragments of human PTH or of rat, porcine or bovine PTH that have human PTH activity as determined in the ovarectomized rat model of osteoporosis reported by Kimmel et al., Endocrinology, 1993, 32(4):1577.

The parathyroid hormone fragments desirably incorporate at least the first 34N-terminal residues, such as PTH(1–34) (SEQ ID NO: 2), PTH(1–37), PTH(1–38) and PTH(1–41). Alternatives in the form of PTH variants incorporate from 1 to 5 amino acid substitutions that improve PTH stability and half-life, such as the replacement of methionine residues at positions 8 and/or 18 with leucine or other hydrophobic amino acid that improves PTH stability against oxidation and the replacement of amino acids in the 25–27 region with trypsin-insensitive amino acids such as histidine or other amino acid that improves PTH stability against protease. These forms of PTH are embraced by the term "parathyroid hormone" as used generically herein. The preferred hormone is human PTH(1–34) (SEQ ID NO: 2) also known as teriparatide. The hormones may be obtained by known recombinant or synthetic methods, such as described in U.S. Pat. No. 4,086,196, incorporated herein by reference. The stabilizing agent incorporated into the solution or composition includes a polyol which includes a saccharide, preferably a monosaccharide or disaccharide, e.g., glucose, trehalose, raffinose, or sucrose; a sugar alcohol such as, for example, mannitol, sorbitol or inositol and a polyhydric alcohol such as glycerine or propylene glycol or mixtures thereof. A preferred polyol is mannitol or propylene glycol. The concentration of polyol may range from about 1 to about 20 wt-%, preferably about 3 to 10 wt-% of the total solution.

The buffering agent employed in the solution or composition of the present invention may be any acid or salt combination which is pharmaceutically acceptable and capable of maintaining the aqueous solution at a pH range of 3 to 7, preferably 3–6. Useful buffering systems are, for example, acetate, tartrate or citrate sources. Preferred buffer systems are acetate or tartrate sources, most preferred is an acetate source. The concentration of buffer may be in the range of about 2 mM to about 500 mM, preferably about 2 mM to 100 mm.

The stabilized solution or composition of the present invention may also include a parenterally acceptable preservative. Such preservatives include, for example, cresols, benzyl alcohol, phenol, benzalkonium chloride, benzethonium chloride, chlorobutanol, phenylethyl alcohol, methyl paraben, propyl paraben, thimerosal and phenylmercuric nitrate and acetate. A preferred preservative is m-cresol or benzyl alcohol; most preferred is m-cresol. The amount of preservative employed may range from about 0.1 to about 2 wt-%, preferably about 0.3 to about 1.0 wt-% of the total solution.

Thus, the present invention has provided, for example, a stabilized teriparatide solution containing mannitol, acetate and m-cresol with a predicted shelf-life of over 15 months at 5° C.

The parathyroid hormone compositions of the present invention may, if desired, be provided in a powder form containing not more than 2% water by weight, that results from the freeze-drying of a sterile, aqueous hormone solution prepared by mixing the selected parathyroid hormone, a buffering agent and a stabilizing agent as above described. Especially useful as a buffering agent when preparing lyophilized powders is a tartrate source. Particularly useful stabilizing agents include glycine, mannitol, sucrose, trehalose, raffinose or a mixture thereof.

The PTH solution and composition of the present invention incorporate PTH in a medically effective amount, a term used with reference to amounts useful either therapeutically or in medical diagnosis. The particular amount of parathyroid hormone incorporated in the preparation can be pre-determined based on the type of PTH selected and on the intended end-use of the preparation. In one application, the preparations are exploited for therapeutic purposes, and particularly for the treatment of osteoporosis. Osteoporosis therapy entails administration of the reconstituted preparation by injection, desirably subcutaneous injection, in unit doses that reflect the prescribed treatment regimen but are, by way of example, for human PTH(1–34) (SEQ ID NO: 2), within the range from 25 µg PTH/mL of injected solution to 1000 µg/ML of injected solution per patient, with injection volumes being desirably from 0.02 to 1.3 mL. Accordingly, the purified PTH is desirably incorporated with the buffering agent and excipient to form an aqueous solution containing PTH in a concentration range from 25 µg/mL to 1000 µg/mL, preferably 100 µg/mL to 500 µg/mL which is then sterile-filtered and filled into a vial or cartridge for use.

Once the preparation is obtained as an aqueous solution containing desired amounts and concentrations of the buffering agent, excipient and PTH, individual vials are filled with the solution to the desired volume. The advantage of the present invention is that the above solution may be prepared with sterile water without the need to undergo a freeze-drying process.

In an alternative embodiment of the invention, the preparations are provided in a form that yields a unit container of 100–500 µg human PTH(1–34) (SEQ ID NO: 2) upon reconstitution into about 1 mL (0.8–1.2 mL) of the reconstitution vehicle, and the vials are accordingly loaded with about 1 mL of the aqueous PTH preparation, for subsequent freeze-drying.

In a preferred alternative embodiment of the invention, the PTH preparation subjected to freeze-drying comprises from 25 to 1000 µg/mL of human PTH(1–34) (SEQ ID NO: 2), from 2 to 8% by weight of mannitol, and a tartrate source in an amount capable of buffering the preparation to within the range from 3.0 to 6.5 upon reconstitution in sterile water. In specific embodiments of the invention, the tartrate buffering agent is incorporated in an amount sufficient to buffer the pH to 3.5 to 5.5.

In addition to their therapeutic use, the present PTH composition can be formulated and administered to aid in medical diagnosis and particularly to assist in establishing the diagnosis of hypoparathyroidism and pseudohypoparathyroidism in hypocalcemic patients. Except for the dose of PTH, the composition of the PTH preparation will remain as described herein for therapeutic use. An intravenously infused, single dose of human PTH(1–34) (SEQ ID NO: 2) that is equal to 200 International Units of PTH activity is appropriate for this diagnostic purpose. Diagnosis is then made by determining the effect of administered PTH or urinary cAMP levels, with cAMP elevation being indicative of the hypoparathyroidism condition rather than its pseudoform.

The examples which follow are illustrative of the invention and are not intended to be limiting.

EXAMPLES

Example 1

0.1 mg rhPTH (1–34) (SEQ ID NO: 2), 50 mg mannitol, 2.5 mg m-cresol, 0.52 mg acetic acid and 0.12 mg sodium acetate were mixed into a solution with 1 ml of distilled water.

Example 2

0.25 mg rhPTH (1–34) (SEQ ID NO: 2), 45.4 mg mannitol, 3 mg m-cresol, 0.41 mg acetic acid and 0.1 mg sodium acetate were mixed into a solution with 1 ml of distilled water.

The formulations of the present invention, Examples 1 and 2 were compared to solutions containing no stabilizer, 0.9% NaCl, 20 mM acetate and 10 mM acetate as primary stabilizer. The stability was measured by determining the amount in % of rhPTH (1–34) (SEQ ID NO: 2) remaining after a certain time. The measurement was made by HPLC. The results are shown in Tables 1 and 2.

TABLE 1

Effect of Primary Stabilizer on Chemical Stability of rhPTH (1–34) at 50° C.

| Time, days | Water | 0.9% NaCl | 20 mM acetate | 10 mM acetate |
|---|---|---|---|---|
| | | % Remaining | | |
| Initial | 100 | 100 | 100 | 100 |
| 7 | 74 | 81 | 84 | 80 |
| 14 | 55 | 58 | 67 | 71 |

TABLE 2

Comparison of Stability of rhPTH (1–34) at 30° C.

| Time, days | 20 mM acetate | 10 mM acetate | Example 1 | Example 2 |
|---|---|---|---|---|
| | | % Remaining | | |
| Initial | 100 | 100 | 100 | 100 |
| 7 | 96 | 94 | 100 | — |
| 14 | 94 | 92 | 96 | 100 |
| 21 | 90 | 93 | 97 | — |
| 30 | — | 81 | 96 | 96 |

Example 3

The following experiment was carried out to show that lyophilized powder formulations prepared from stabilized solutions of the present invention are more stable than a control which was prepared from PTH(1–34) and mannitol alone.

A control solution and solutions for samples A through O were prepared as previously described with the ingredients and concentrations shown in Table 3. The solutions were then freeze-dried and the resulting lyophilized powder formulations were stored at 40° C. for a one month period. The amount of PTH(1–34) remaining in each sample was then measured by HPLC. The results are shown in Table 3.

TABLE 3

Stability of PTH(1-34) Lyophilized Formulations at 40° C. for One Month

| Sample | PTH(1-34) mg/mL | Bulking Agent | Bulking Agent Conc. mg/mL | Buffer | Buffer Conc. mM | % PTH Remaining |
|---|---|---|---|---|---|---|
| Control | 0.2 | mannitol | 40 | — | — | 78 |
| A | 0.5 | mannitol | 30 | acetate | 5 | 90 |
| B | 0.5 | glycine | 30 | acetate | 5 | 98 |
| C | 0.5 | sucrose | 30 | acetate | 5 | 98 |
| D | 0.5 | trehalose | 30 | acetate | 5 | 97 |
| E | 0.5 | raffinose | 30 | acetate | 5 | 99 |
| F | 0.75 | mannitol | 30 | tartrate | 15 | 95 |
| G | 1.5 | sucrose & mannitol | 5/25 | tartrate | 5 | 99 |
| H | 0.75 | sucrose & mannitol | 5/25 | tartrate | 15 | 99 |
| I | 1.5 | mannitol | 30 | tartrate | 5 | 96 |
| J | 1.5 | sucrose | 30 | tartrate | 15 | 100 |
| K | 1.5 | mannitol | 30 | tartrate | 15 | 99 |
| L | 0.75 | sucrose | 30 | tartrate | 15 | 100 |
| M | 0.75 | sucrose | 30 | tartrate | 5 | 100 |
| N | 1.5 | sucrose & mannitol | 5/25 | tartrate | 15 | 99 |
| O | 1.5 | sucrose & mannitol | 5/25 | acetate | 5 | 91* |

*the stability at 2 months was 96%

We claim:

1. An aqueous pharmaceutical solution, which comprises: human parathyroid hormone (1–34) in a concentration of about 100–500 ug/ml; an acetate buffer to maintain the pH range of the solution from 3 to 6; a stabilizing agent selected from the group consisting of glucose, trehalose, raffinose, sucrose, mannitol, sorbitol, inositol, glycerine, propylene glycol, and mixtures thereof; a parenterally acceptable preservative; and water; wherein said solution is sterile and ready for parenteral administration to a human patient.

2. The pharmaceutical solution of claim 1 wherein the preservative is selected from m-cresol or benzyl alcohol.

3. The pharmaceutical solution of claim 2 wherein the preservative is m-cresol at a concentration range of about 0.3 to about 1.0% by weight of the solution.

4. The pharmaceutical solution of claim 1, 2, or 3, wherein the stabilizing agent is mannitol at a concentration of about 3% to 10% by weight of the total solution.

5. The pharmaceutical solution of claim 1, 2, or 3 wherein the concentration of the buffer is in the range of about 2 mM to 100 mM.

6. The pharmaceutical solution of claim 5 wherein the buffer includes acetic acid and sodium acetate.

7. The pharmaceutical solution of claim 1, 2, 3, or 4, wherein said parathyroid hormone concentration is 250 ug/ml.

8. An aqueous pharmaceutical solution, which comprises: 0.25 mg human parathyroid hormone (1–34), 50 mg mannitol, 2.5 mg m-cresol, 0.52 mg acetic acid and 0.12 mg sodium acetate mixed per 1 ml of water, wherein the solution is sterile and ready for parenteral administration to a human patient.

9. A method for preparing a sterile, ready to administer pharmaceutical solution for parenteral administration comprising human parathyroid hormone (1–34), said method comprising the steps of:
   a) admixing human parathyroid hormone (1–34) with: an acetate buffer to maintain a pH range from greater than 3 to less than 7; a stabilizing agent selected from the group consisting of glucose, trehalose, raffinose, sucrose, mannitol, sorbitol, inositol, glycerine, propylene glycol, and mixtures thereof; a parenterally acceptable preservative; and water wherein said parathyroid hormone is at a concentration of about 100–500 ug/ml; and
   b) sterilizing the solution for parenteral administration without undergoing a step of freeze-drying or reconstitution prior to use by a patient.

10. The method of claim 9, wherein the preservative is m-cresol in a range of about 0.3 to about 1.0% by weight of the solution; the stabilizing agent is about 3 to 10% by weight of the total solution; and the concentration of the buffer system is in the range of about 2 mM to 100 mM.

11. The method of claim 10, wherein about 0.25 mg human parathyroid hormone (1–34), 50 mg mannitol, 2.5 mg m-cresol, 0.52 mg acetic acid and 0.12 mg sodium acetate are mixed per 1 ml of water.

12. A sealed vial comprising:
   a sterile, aqueous pharmaceutical solution ready for parenteral administration to a patient, said solution comprising human parathyroid hormone (1–34) in a concentration range from 100 ug/ml to 500 ug/ml; an acetate or tartrate buffer system to maintain the pH range of the solution from 3 to 6; a stabilizing agent selected from glucose, trehalose, raffinose, sucrose, mannitol, sorbitol, inositol, glycerin, and propylene glycol, or mixtures thereof; a parenterally acceptable preservative; and water; wherein said solution has not been reconstituted in the vial from a powder.

13. The sealed vial of claim 12 wherein the stabilizer is mannitol.

14. The sealed vial of claim 13 wherein the parathyroid hormone (1–34) is at a concentration of 250 ug/ml, the mannitol is at a concentration of about 1% to about 20% by weight of the solution, and the preservative is at a concentration of about 0.1% to about 2% by weight of the solution.

15. A sealed vial as in claim 14 wherein said preservative is selected from m-cresol or benzyl alcohol and the mannitol is at a concentration of about 3 to 10% by weight of the solution.

* * * * *